(12) United States Patent
Prichep

(10) Patent No.: US 7,016,722 B2
(45) Date of Patent: Mar. 21, 2006

(54) SYSTEM AND METHOD FOR FETAL BRAIN MONITORING

(75) Inventor: Leslie S. Prichep, Mamaroneck, NY (US)

(73) Assignee: New York University, New York, NY (US)

( * ) Notice: Subject to any disclaimer, the term of this patent is extended or adjusted under 35 U.S.C. 154(b) by 229 days.

(21) Appl. No.: 10/377,967

(22) Filed: Feb. 28, 2003

(65) Prior Publication Data

US 2003/0144601 A1 Jul. 31, 2003

Related U.S. Application Data

(63) Continuation-in-part of application No. 09/716,517, filed on Nov. 20, 2000, now Pat. No. 6,556,861.

(51) Int. Cl.
*A61B 5/04* (2006.01)

(52) U.S. Cl. .......................................... 600/544; 607/902
(58) Field of Classification Search ................. 600/453, 600/511, 544, 559; 381/151; 73/585; 607/902
See application file for complete search history.

(56) References Cited

U.S. PATENT DOCUMENTS

| | | | |
|---|---|---|---|
| 5,003,986 A | | 4/1991 | Finitzo et al. |
| 5,023,783 A | * | 6/1991 | Cohen et al. ............... 600/559 |
| 5,601,091 A | | 2/1997 | Dolphin |
| 5,913,834 A | | 6/1999 | Francais |
| 6,556,861 B1 | * | 4/2003 | Prichep ...................... 600/544 |

FOREIGN PATENT DOCUMENTS

| | | |
|---|---|---|
| EP | 0 437 012 A1 | 7/1991 |
| WO | WO 00/64351 | 11/2000 |

OTHER PUBLICATIONS

Staley et al. "The Human Fetal Auditory Evoked Potential". 1990. Electroencephalography and clinical Neurophysiology, 77: 1–5.*

Eswaran et al. "Brain Stem Auditory Evoked Potentials in the Human Fetus During Labor". AmJ Obstet Gynecol. vol. 180, No. 6, Part 1; 1422–1426.*

* cited by examiner

*Primary Examiner*—Max F. Hindenburg
*Assistant Examiner*—Jonathan Foreman
(74) *Attorney, Agent, or Firm*—Fay Kaplun & Marcin, LLP

(57) ABSTRACT

A system for monitoring a brain wave response of a fetus in utero, comprises removably connecting an auditory transducer, including at least one biosensor electrode, producing pulsed auditory sounds to a mother's abdomen to detect brain wave activity in a fetus. The transducer is pulsed with one of rectangular waves and tone pips of a selected frequency to emit pulsed audible sounds at predetermined times. The at least one biosensor electrode, including connected amplifier, detects brain stem auditory responses (BAER) of the fetus. For each pulsed audible sound a series of voltage oscillations corresponding to BAER of the fetus are time-locked to the corresponding audible sound. BAER analog output is converted to BAER digital data. A computer-based QEEG (Quantitative EEG) system improves a signal to noise ratio of the BAER digital data using an adaptive optimum filtering algorithm and analyzes the BAER digital data relative to a reference database.

22 Claims, 3 Drawing Sheets

US 7,016,722 B2

SYSTEM AND METHOD FOR FETAL BRAIN MONITORING

PRIORITY CLAIM

This application is a Continuation-in-Part of U.S. patent application Ser. No. 09/1716,317 filed Nov. 20,2000, entitled "Fetal Brain Monitor" ("the '517 applications"), now U.S. Pat. No. 6,556,861. The entire disclosure of the '517 application is expressly incorporated heroin by reference.

FIELD OF THE INVENTION

The present invention relates to medical obstetric procedures and devices and more particularly to the non-invasive monitoring of the human fetus while in the mother's uterus.

BACKGROUND INFORMATION

It is conventional, in medical practice to ascertain the status and health of a human fetus by ultrasound. Typically a pregnant female may undergo 1 to 4 ultrasound examinations during her pregnancy. In addition, the heart of the fetus will be detected and monitored using a stethoscope. It is also conventional to monitor the heartbeat of a neonate (newly born infant) during and immediately after childbirth, using a stethoscope or a more sophisticated analysis instrument.

After childbirth, the status of pre-term neonates may also be ascertained using electroencephalography ("EEG"), which measures neurophysiological activity, which is essentially a pattern of electrical signals generated by the brain, known generally as brain waves. The EEG comprises a record of electrical rhythms and other electrical activity of the brain. EEG's are widely used to assist in the diagnosis, in children and adults, of epilepsy, brain tumors, physiological disorders and other brain abnormalities. An EEG examination may disclose and help diagnose brain abnormalities and injuries such as those described above because an injured or abnormal brain will produce electrical waves that differ in predictable ways from waves produced by a normal and healthy brain.

It has been thought to be very difficult to obtain meaningful brainwaves from fetuses because the fetal brain produces brain waves that are weaker than those of a child or an adult and the signals must traverse multiple layers of tissue that enclose the fetus (e.g., amniotic fluid, mother's layers of skin, muscle and blood).

SUMMARY OF THE INVENTION

The present invention is directed to a method of monitoring a brain wave response of a fetus in utero, comprising the steps of removably connecting an auditory transducer at least one biosensor electrode to a mother's abdomen to detect brain wave activity in a fetus therein and pulsing the transducer with one of rectangular waves and tone pips of a selected frequency to emit pulsed audible sounds at predetermined times in combination with the steps of detecting, for each pulsed audible sound, a series of voltage oscillations corresponding to brain stem auditory evoked responses (BAER) of the fetus which are time-locked to the corresponding audible sound and converting the BAER analog output to BAER digital data.

The present invention is further directed to a Fetal Brain Monitor for monitoring a brain wave response of a fetus in utero, comprising an auditory transducer producing pulsed audible sounds and adapted to be placed on an abdomen of a mother of the fetus and at least one biosensor electrode adapted to be placed on the mother's abdomen for detecting electrical activity of a brain of the fetus in combination with a pulsing arrangement pulsing the transducer with one of rectangular waves and tone pips of a selected frequency so that it emits pulsed audible sounds at predetermined times and an amplifier connected to the at least one biosensor electrode to amplify brain stem auditory responses (BAER) of the fetus detected by the at least one biosensor electrode which are time-locked to the sounds. An analog/digital converter converts the analog BAER data to BAER digital data, a computer-based QEEG (Quantitative EEG) system improves a signal to noise ratio of the BAER digital data and analyzing the BAER digital data.

BRIEF DESCRIPTION OF DRAWINGS

The following detailed description is of the inventor's presently known best mode of practicing the invention and should be taken in conjunction with the accompanying drawings wherein.

DETAILED DESCRIPTION

In accordance with the present invention, the brain waves of a fetus are detected using non-invasive means and analyzed using a Fetal Brain Monitor ("FBM"). This is a very difficult procedure and requires highly sophisticated techniques and sensitive equipment. However, the evaluation of fetal brain waves may permit the assessment of conditions which may lead to abnormal or delayed intrauterine development and provide a standard for normal fetal development. Those skilled in the art will understand that, while the invention is described in regard to the detection of brain waves from a human fetus, the same apparatus and methods may be applied to detect brain waves of other species.

Figure 1:
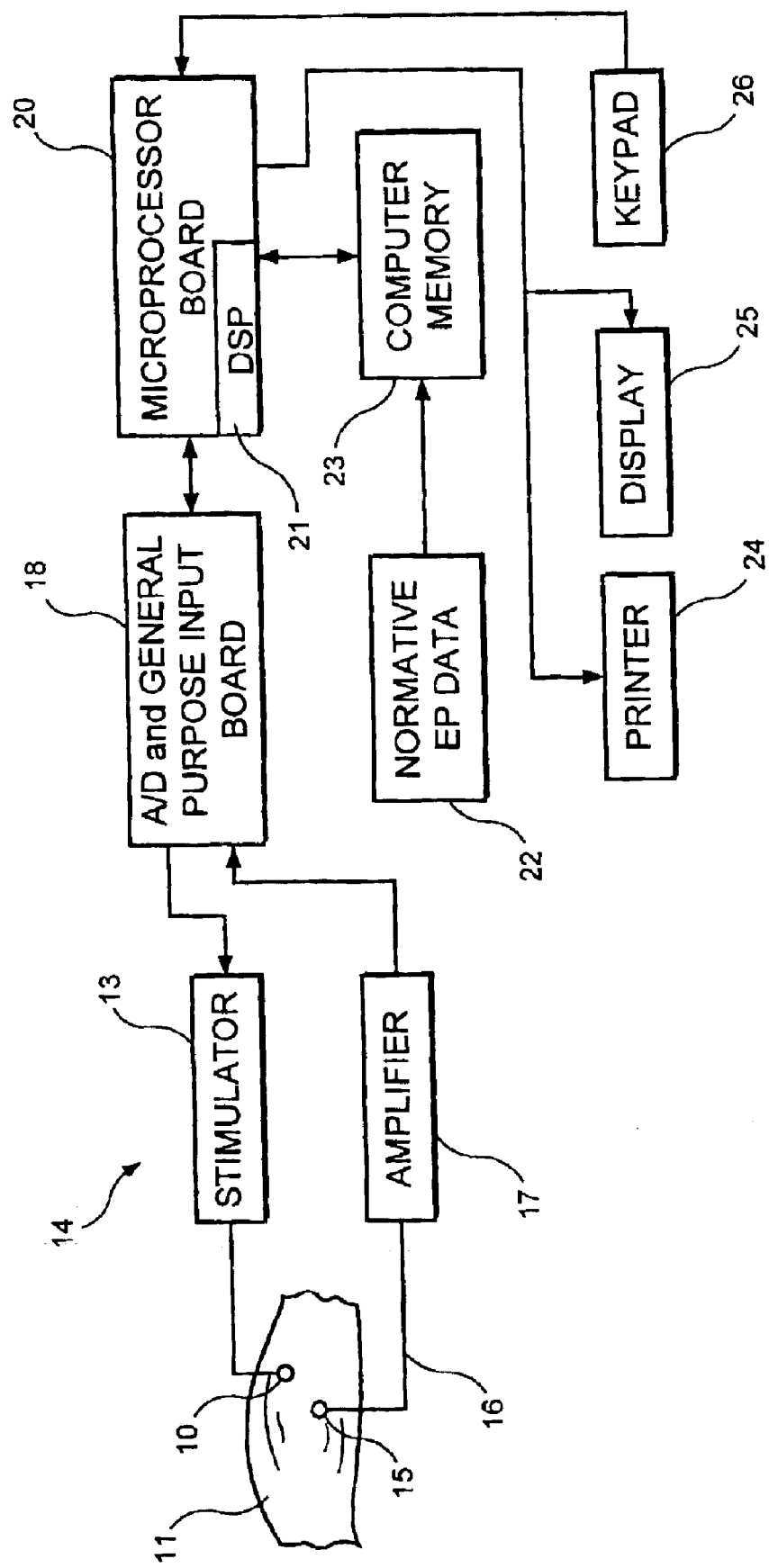
FIG. 1 is a block circuit diagram of the Fetal Brain Monitor ("FBM") of the present invention.

FIG. 1 shows a Fetal Brain Monitor ("FMB") 14, which is used to non-invasively obtain BAER data from a fetus in-utero. BAER data may be obtained from a fetus when it has developed sufficiently to hear and respond to auditory stimuli, which usually occurs when the fetus has become viable or in the third trimester of pregnancy. In order to detect fetal brain waves which are very faint, it is preferred that they be timed in response to stimuli, preferably auditory stimuli. A sound generator that, for example, produces clicking sounds, is placed on the belly of a pregnant woman. The clicking sounds are transmitted through her skin, muscles, womb and amniotic fluid, to the ears of the fetus. Transmission of the clicking sounds is possible because sound travels well through fluids.

The FBM 14 comprises an auditory stimulus transducer 10 that may be removably positioned on the skin of the abdomen 11 of a pregnant human female. The transducer 10 may be similar to those used to generate ultrasonic sounds in an ultrasound fetal examination, except that it operates in the auditory range (e.g., below 15,000 Hz). In a preferred embodiment the transducer 10 consists of a small audio loudspeaker, which is driven by a stimulator 13 and is physically coupled, at one end, to a cylinder filled with saline solution, with the other end covered by a thin rubber membrane.

The rate, amplitude, and duration of the sound pulses generated by the transducer 10 may be preferably similar to those used for BAER monitoring of children and adults. The transducer 10 may deliver a variety of sounds; or in another embodiment, vibratory stimulation, generated by mechanical tapping of the abdominal wall. The transducer 10 delivers the required sound energy to the skin in pulses at an optimal frequency, given the mechanical compliance of the transducer system (i.e., the speaker coupled to the fluid-filled cylinder). The transducer 10 may be pulsed with rectangular waves or tone pips of optimal frequency. This optimal frequency is a limiting factor on the speed with which BAER may be acquired from a fetus. FIG. 1 also shows a single biosensor electrode 15, which is removably placed on the abdomen 11 to detect fetal brain waves, preferably several centimeters from the transducer 10. Those skilled in the art will understand that one or more of the electrodes 15 may be employed to detect fetal brain waves. The electrode 10 may be a pre-gelled self-adhesive sterile disposable electrode. Such electrodes do not require skin preparation or collodion and should provide a low electrical impedance (under 5000 ohms). The electrode 10 attaches to a reusable lead wire 16 and is an alternative to a conventional EEG cup electrode setup.

In an alternative embodiment, the electrode 10 may have multiple small barbs, a needle or a conductive disk, which is removably attached by slightly penetrating skin of the abdomen's 11 skin. For example, the Zip-Prep electrode, which has stainless micro-barbs and an adhesive gel patch, may be used. The electrode 10 may also use conductive gel, which allows for rapid attachment and acceptably low noise.

The lead wire 16 to which the electrode 10 is attached is connected to a high-gain low-noise amplifier 17, which may be battery powered and which amplifies analog brainwaves. As the required amplification of the signals is greater than with conventional EEG amplifiers because of the faintness of the signals, the amplifier 17 may, for example have a resolution of 50 nanovolts at the least significant bit of the A/P conversion and a high input impedance (e.g., approximately 10 Megohms), a bandwidth of 200 Hz to 5000 Hz, and a noise level of less than $0.5\mu$ rams and produces an analog output signal. The amplifier 17 also has an input isolation circuit to protect against current leakage, such as a light-emitting diode (LED) isolation coupler. The amplifier 17 is protected from electrical interference by a radio-frequency filter and a 60-cycle notch filter. The amplifier 17 is connected to an analog-digital converter 18 and a multiplexer within the General Purpose Input Board ("GPIB") 18 which converts the analog signals received from the amplifier 17 to digital signals. The analog-digital converter 18 operates at a minimum rate of 20,000 samples per second and a resolution of 16 or more bits.

The analog-digital converter 18 is connected to a software programmed microprocessor board 20, which has a central processing unit ("CPU") 19 and a digital signal processor ("DSP") 21. A computer memory 23, which includes both ROM and RAM types of memory is also connected to the microprocessor 20. As would be understood by those of skill in the art the CPU 19, the microprocessor 20, DSP 21, and the computer memory 23 may be portions of any computer system (e.g., a laptop, a PC, a handheld, etc.). The microprocessor 20 is programmed to perform data acquisition and data analysis as described below. The microprocessor 20 may be programmed by external software program means, such as a floppy disk recorder, or another input system, such as ROM. The microprocessor 20 may be, for example, a conventional microprocessor, such as an Intel Pentium IV, and the memory 23 may, for example be, any internal memory, for example, 1 Gigabyte of hard-drive space and 512 Megabytes of RAM. The memory 23 contains normative evoked potential ("EP") data 22, which is stored in a database and is used by the computer system to perform functions described below. The CPU 19, the microprocessor 20, and DSP 21 provide a timed sequence of audio simulation, such as a rectangular wave or tone pips repeated at optimal frequency Fi in order to pulsate the transducer 10. The computer system also analyzes the BAER data to determine the functional state of the fetal brain stem.

For inputting and outputting data, for example, a printer 24, a display 25, and a keypad 26 may also be connected to the microprocessor 20. As would be understood by those skilled in the art, the keypad 26 is used to communicate with the microprocessor 20 and the display 26 and the printer 24 show the results of the analysis. A series of such reports from the same fetus may be assembled to give a picture of brainstem development longitudinally during gestation or of momentary brain states, for example, during stages of delivery.

Method Overview

The FBM 14 audio-stimulates the fetus by using the stimulator 13 under control of the microprocessor 20, which automatically times the set of auditory stimuli. The fetus' brainwaves in the EEG will respond to each stimulus at repetition rate Fi with a component at frequency Fi, Fi providing an EP. Those brainwaves may be averaged and time-locked to stimuli onset to improve the signal-to-noise ratio, to generate a Brainstem Average Evoked Response ("BAER"). The BAER is the sum of N brainwaves time-locked to the onset of stimuli divided by N, the number of samples, to provide an updated average. N will vary depending upon the sensory modality. The BAER's are stored in the memory 23.

For testing, with the subject comfortably seated or lying down in a reclining position, the stimulator 13 will be placed on the mother's abdomen 11 and the electrode 15 will be placed at a point near the head of the fetus as determined by an obstetrician. A reference electrode may then be pasted on the mother's thigh. The intensity levels of auditory stimulation are preferably within the range of levels used in other routine prenatal examinations (e.g., sonograms). Normative waveshapes may be standardized at any desired interval, providing a developmental brainstem evaluation during pregnancy or a monitor of brainstem state during labor and delivery.

The analysis of the EEG is performed using advanced filtering techniques and algorithms relating to Quantitative EEG ("QEEG"). These techniques are critical to obtaining meaningful data from the faint electrical brain waves of the fetus. For example, the fetus in the embryonic sac is in almost constant movement, which along with the heartbeat of the fetus, generates noise that may drown out the brainwave data. The maternal environment also generates noise in addition to noise generated by movement of the fetus. This noise includes the heartbeat of the mother, movements of the mother—muscle artifacts (e.g., breathing, eye blinking, etc.) and the mother's brain waves, including the mother's brain wave response to the auditory stimuli. As indicated by prior studies, the voltages, generated by these sources of noise may be larger than that generated by the fetal brain. The following are some of the quantitative approaches to improve the signal-to-noise ratio in this difficult EEG environment.

Preferably the fetal brainwaves, after analog-to-digital conversion, are subjected to "optimal digital filtering." Such filtering quickly removes contaminating noise. A digital comb filter may be used to reduce the adverse effects of noise, as disclosed in U.S. Pat. No. 4,705,049, the entire disclosure of which is hereby incorporated by reference. Filtering and splitting algorithms may reduce low-frequency noise and remove artifact-contaminated samples prior to averaging. In the alternative, other methods for enhancing signal-to-noise ratios may be used, such as very narrow band ("VNB") fast fourier transform ("FFT") at a repetition rate Fi equal to that of the auditory stimulus. In the present embodiment, VNB FFT would be performed on successive samples and the power at each frequency would be averaged across the set of samples. Power in the FFT at the frequency Fi is indicative of the fetal brain response to the auditory test probe. While this method would not provide wave shape details, it would provide an indication of the responsivity of the fetal auditory system. Digital filtering is discussed in more detail below.

One method of removing artifactual contamination is to gather only specific brainwaves selected according to the following calculations. An updating voltage threshold is computed continuously for the EEG channel or, if there is more than one channel, separately for each channel by calculating a root mean squared ("RMS") voltage in a sliding window, for example, 20 seconds long. The RMS voltage is approximately 0.2 standard deviations of the mean amplitude. An amplitude threshold is set, usually at about 16×RMS, which will be exceeded by chance about 0.1% of the time. Segments containing voltages at any time point which are larger than this updated threshold would then be rejected unless the operator of the FBM 14 chooses not to use this option. Sampling is then suspended for a short period of time (e.g., 1 second) to avoid increasing the threshold by incorporating the artifact, after which time period the sampling is resumed. Preferably, as a result of the above computations, intervals (the recording periods on each EEG channel) in which the voltage exceeds a multiple of the RMS voltage equal to 3.2 times the standard deviation of the amplitude are rejected. Alternatively, an absolute maximum voltage threshold may be installed. This voltage threshold method selects segments of relatively artifact-free EP data for further analysis. The computer system combines these intervals together to form a continuous artifact-free EP sample, which is recorded by the microprocessor 20.

Many critical decisions may depend on the accuracy of the data collected by the FBM 14. Therefore it is important to construct at least two EP data samples to double check the results of the examination. Preferably three interlocked, but independent samples are constructed and compared for replicability.

For example, two split-half but independent samples, each containing 32 light averages, each being the sum of 64 stimuli, are constructed by alternatively assigning single evoked potentials to each sample, $\Sigma V_1$ and $\Sigma V_2$ The standard deviation ($\sigma$) within each such sample can be computed at each sample point of the light averages; $\sigma^2=(\Sigma V^2/N)-(\Sigma V/N)^2$, where V is the voltage at each time point; then squared mean $(V/N)^2$ is subtracted from the mean square $V^2/N$. For a true dysfunction to be shown by the above calculations, they must be reliable. Reliability is determined by testing the replicability of the samples using the t-test at each point according to the formula: $t=(V_1-V_2)/|\sigma^2_{(v1)}+\sigma^2_{(v2)}|^{1/2}$. Alternatively, it is also possible to use a cross-correlation across the entire wave with a threshold for minimum correlation, which would be acceptable to replicate replicability. Once normative data are available for the mean values of the voltages at every time point, as a function of gestational age, this method can be used to test whether a fetal BAER is outside normal limits. If an abnormality is found in both split-half samples each with a significance of P>0.05, for example, replication yields $P^2<0.0025$. Results from the two split halves may be combined by averaging them. In addition, the replicated significant results may be highlighted.

"Neurometric" analysis is also applied to determine whether EEG power at any frequency or the amplitude or latency of each peak in the fetal brain wave or BAER waveshape is within the limits defined by the distribution of values in a control reference database. Neurometric analysis is a statistically based set of techniques and algorithms, which collects data from control groups of normally developing fetuses. Data from the fetus being monitored at each state of fetal development is then compared to data from the control group to ascertain whether the data indicates that the BAER is normal. If the data indicates that the BAER is abnormal, the analysis can indicate the extent and nature of the abnormality. In another embodiment, the state of the fetal brain is assessed relative to an initial state in the fetus and the fetal data serves as its own "self-norm." Such self-norming allows comparison of successive measurements to data from prior states.

Brainstem Auditory Evoked Responses

BAER are time-locked to the auditory stimuli. Preferably the responses are in the interval of 1–10 milliseconds (MS) after the presentation of the stimulus. This time period is sufficiently long for the FBM 14 to receive data regarding the perturbation of brain electrical rhythms following an auditory stimulus. In addition, the timing (latency) of the peak responses from each portion of the brain stem relative to the stimulus presentation is known, so that data which falls outside of the expected range may be discarded.

Figure 2:
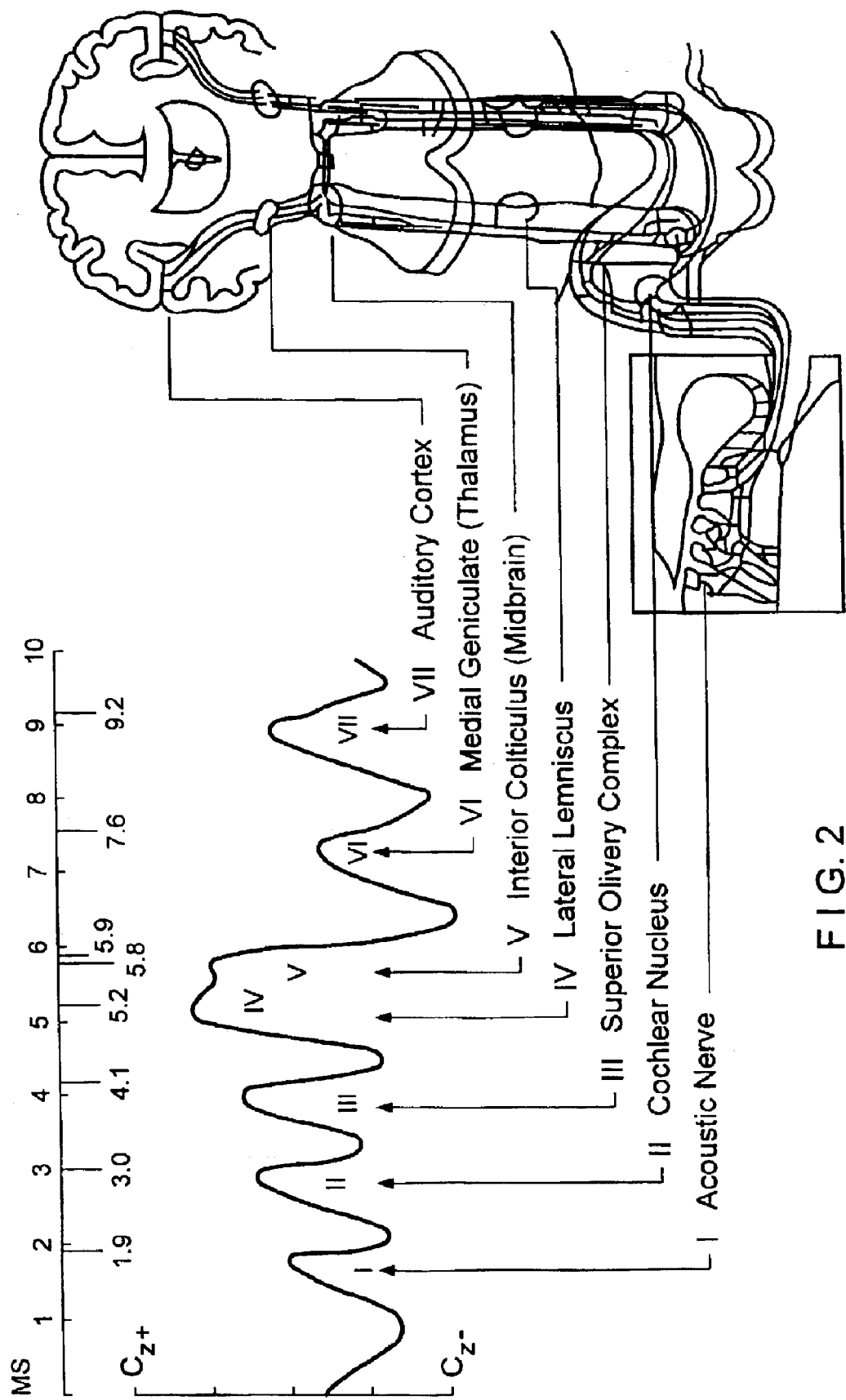
FIG. 2 is a chart showing normal Brainstem Auditory Evoked Response ("BAER")
Figure 3:
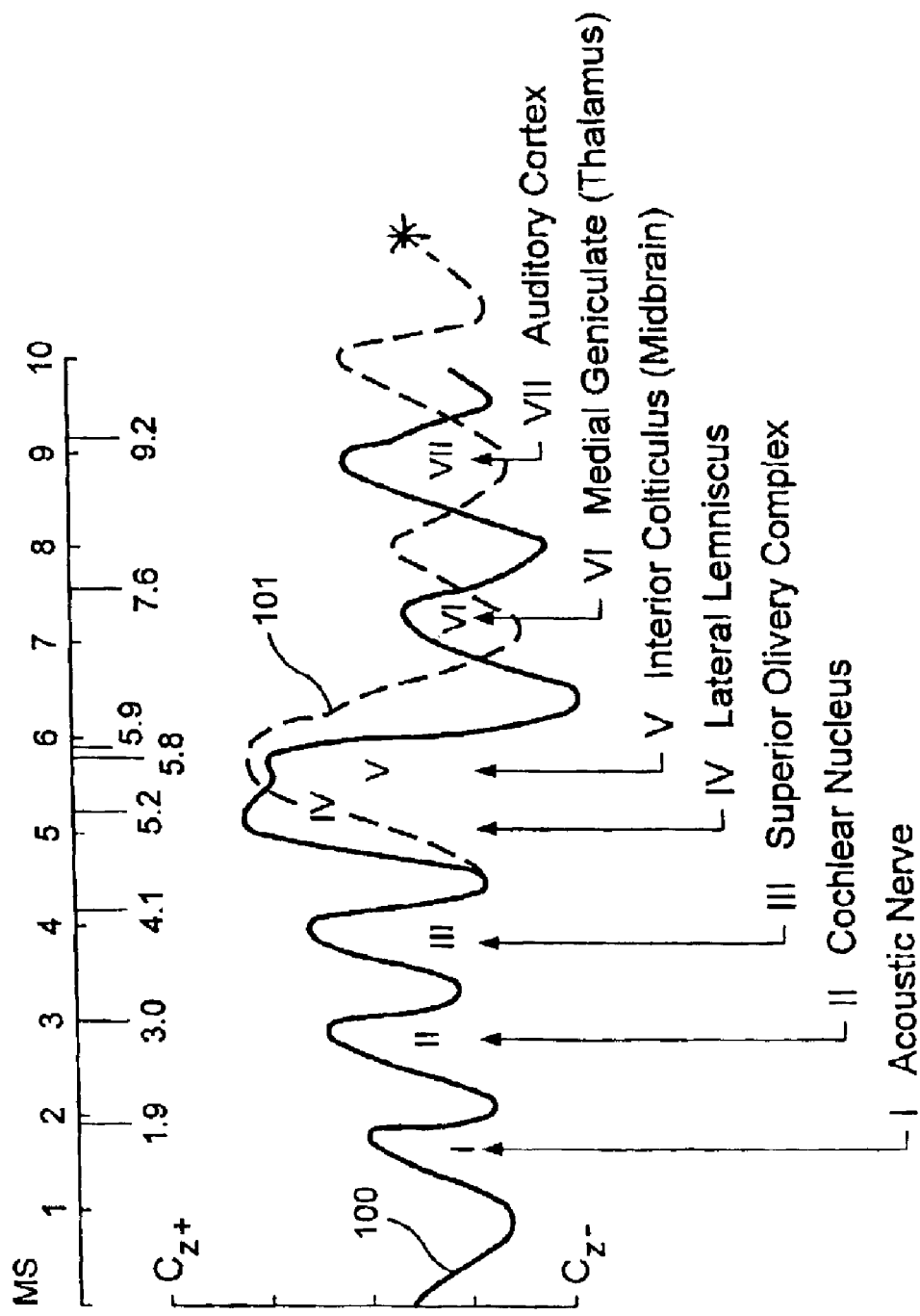
FIG. 3 is a chart comparing normal and abnormal BAER's.

The latencies, which are the elapsed times of the peaks of the BAER waveshape, reflect the transmission along the auditory pathway of neural electrical brain wave volleys, which are time-locked to the auditory stimuli. FIG. 2 shows a BAER diagram. Each peak in the diagram reflects the arrival of a volley of impulses at a successive level of the auditory pathway—specifically the auditory nerve ($7^{th}$ cranial nerve), dorsal cochlear nucleus, superior olivary complex, lateral lemniscus, inferior colliculus, medial geniculate and the auditory cortex. FIG. 3 shows a normal BAER 100, represented as a solid line and an abnormal BAER 101, represented as a dashed line. The transmission times provide an estimate of the functional status of the neural structures and connecting pathways, and reflect complex factors (e.g., level of certain chemicals within the neural structure), which influence the level of polarization of the neuronal membrane and the availability of neuronal transmitters. Thus, the latencies of successive BAER provide functional estimates for the corresponding regions of the brainstem.

Normative studies have shown the mean latencies of these peaks, and the inter-peak intervals, of the BAER of an infant to be precisely predictable and to stabilize at about 2 years of age to the characteristic adult values, with very small fluctuations (in the order of 200 microseconds for every peak) from age-appropriate normative values. Therefore, the assessment of peak latencies has been found to have clinical implications in a wide variety of brain dysfunctions. However, such norms do not presently exist for mean latencies of the peaks of BAER of a fetus in-utero.

The maturational changes in BAER morphology, especially the very rapid changes within the first months of life, may provide an invaluable means for monitoring and following the development of the central nervous system. In addition, BAER of fetuses may be used as an early diagnostic tool in obstetrics. Studies have shown consistent differences between pre-term and full-term neonates, often correlated to lesions or dysfunction of the peripheral and/or central auditory system or more extensive dysfunction which resulted from outside influences on the developing brain (Taylor, Pasman, Singh). Many of the deviations from BAER norms found in premature and other high-risk infants may have been present in the fetus. This detection of such deviations from BAER norms in-utero may provide an objective method for early central nervous system assessment and prognosis and eventual effective early intervention and remediation.

Optimal Digital Filtering

In signal averaging, a transducer 10 usually produces 2048 auditory clicks at a rate of 5–20 per second. These responses are averaged and the noise is reduced proportionally to the square root of the number of stimuli. This signal averaging procedure is relatively slow. Since ambient noise can be up to 10–20 microvolts, based on the earlier example a 1/2048 would reduce the noise to about 200–400 nanovolts. The signal-to-noise ratio is unfavorable using conventional averaging, because the BAER of the fetus will be only about 100–200 nanovolts. In one embodiment, FBM 14 utilizes a digital comb filter to improve the signal-to-noise ratio. As described above, a suitable digital comb filter is described in U.S. Pat. No. 4,705,049. In such a filter, the band pass frequencies are automatically selected to form the teeth of the comb, using a phase variance parameter. That phase variance parameter is computed in the presence and absence of audio stimuli. Optimal digital filtering maybe used as an alternative to signal averaging to improve signal-to-noise ratio.

Two samples of EEG data are collected, one in the presence of auditory stimulation (signal) and one in the absence of stimulation (noise). Both samples are comprised of an adaptively determined sufficient number of trials, "light averages," for example 20, where each light average is an average of an adaptively determined sufficient number of EEG segments for example 100, each segment being 10 milliseconds in duration, sampled at least every 50 microseconds. The auditory stimulus immediately precedes each of the "signal" segments, in which the BAER is embedded, but no stimulus is presented before the "noise" segments. Both "signal" and "noise" samples are first constructed in the time domain. Each of the trials in the two samples may then be subjected to spectral analysis using, e.g., 512-point Fast Fourier Transform ("FFT") the first 200 points may span the analysis epoch of the BAER, for example 10 milliseconds, and the remaining 312 points are set to the mean value of the initial 200 points.

An amplitude and a phase of each spectral component is obtained for each of the trials. The mean amplitude and the phase variance across the trials are then computed for every spectral component, separately for the "signal" trials, $\Sigma_s^2$, and the "noise" trials, $\Sigma_N^2$. For each spectral component, the F ratio of phase variance in the "signal" trials to the phase variance in the "noise" trials is computed, where $F=\sigma_s^2/\sigma_N^2$. A threshold is set for each frequency, so that the probability of the F ratio if signal information is present is equal to the P=0.01 level. If F reaches this level of statistical significance (i.e., P>0.01), there is significantly less variance at that frequency in the presence of stimulation than in the ambient electrical noise. A responsive auditory system must display such significance in successive latency intervals, corresponding to the transmission speed along the auditory pathway. At least the earliest peak must be present with such significance, in order to confirm auditory responsivity. If, after an initial number of trials, this level of significance is not obtained, the number of trials in each light average is increased and the process is repeated until the statistical probability is reached. If acceptable significance is not reached when the number of trials in each light average reaches a critical sample size, such as e.g. 2048 samples, the auditory system may be considered to be unresponsive. Those specific spectral components for which this F ratio indicates that phase variance is significantly lower in the "signal" samples than in the "noise" samples, are identified to contain phase-locked information about the stimulus. Based upon this analysis, coefficients of frequency components where there is not significantly more information in the signal samples than in the noise samples are set to 0, and an Inverse Fast Fourier Transform ("IFFT") is performed on each of the trials in the "signal" sample, using, e.g., the same 512-point FFT. This reconstructs the BAER in the time domain with the noise contamination selectively removed.

After digital filtering and IFFT have been performed, the mean amplitudes and variances of the amplitude at each sampling point (latency) are computed across the optimal number of signal light averages. This mean amplitude curve is the waveshape of the digitally filtered BAER. This waveshape is expected to have no more than five peaks at least 0.8 milliseconds apart (referred to as Peaks I to V).

The latencies of the successive peaks of the BAER thus smoothed by digital filtering are determined, using the zero crossing of the first derivative or directly from the 512-point FFT. If necessary, 3-point smoothing of the filtered BAER may be used to reduce the number of peaks thus detected to no more than the five major peaks of the normal BAER, with no two peaks closer than a minimum permitted inter-peak interval (e.g., 0.80 milliseconds).

Another method of smoothing the filtered BAER is to compute a coefficient of variation ("CV") where CV=variance/mean amplitude, at each sample point within the 10 millisecond latency epoch, across the 20 smoothed BAER light averages in the signal sample. The values of CV will be minimal and the first derivative of a graph of CV vs. latency will be zero at the latencies of the successive BAER peaks.

The entire collection and analysis process of BAER evaluation is preferably performed at least twice (split halves, odd and even), in order for the resulting waveshapes to be clinically accepted as valid BAER estimates. Validation of BAER estimates requires that some of the peaks in the two iterated analyses be congruent within a permitted latency margin, such as 2 or 3 sample points. Threshold values of CV, installed in the FBM 14, may serve as criteria to determine whether generated BAER estimates are valid.

If a true dysfunction exists, the measures revealing it must be reliably predictable. Replicability can be tested using the t-test at each time point by using the following formulae. In an alternative embodiment, the BAER of the fetus will be computed by presentation of accumulation of three sets of samples: signal 1 ("s1"); signal 2 ("s2"); and noise ("n"). Each sample will be at least 10 milliseconds in duration, sampled at 50 microsecond intervals. For each sample at each time point, the sum of the voltage ($\Sigma V$) and the sum of the squared voltage ($\Sigma V^2$) is calculated. As the sample size N is increased, the following quantities are continuously calculated at each sample point:

$$t_{s1,n} = (s1-n)/|\sigma^2_{(s1)} + \sigma^2_{(n)}|^{1/2}$$

$$t_{s2,n} = (s2-n)/|\sigma^2_{(s2)} + \sigma^2_{(n)}|^{1/2}$$

$$t_{s1,s2} = (s1-s2)/|\sigma^2_{(s1)} + \sigma^2_{(s2)}|^{1/2}$$

Five latency intervals are specified from 0–10 milliseconds, corresponding to the inter-peak latencies of the five expected peaks of the BAER, as exemplified in Table 1 below, with allowance for slowing caused by dysfunction or immaturity. The process of collecting and evaluating data continues until the differences $t_{s1,n}$ and $t_{s2,n}$ exceed the P<0.01 level of significance for at least three successive sample points within the permitted latency intervals, with no such significant differences for $t_{s1,s2}$. When a total of 10 minutes of auditory stimulation has elapsed without these criteria being MET, the absence of BAER will be concluded.

This optimal filter is applied to extract the BAER from brief samples of data. This permits real time monitoring, with rapid updates, which may be desirable during labor. This procedure may enable clean BAER waveshapes to be updated every 5 seconds with clearly defined peaks, using stimulus repetition rates as high as 35 per second.

Data Evaluation

Data evaluation uses a quantitative assessment of the age-expected normality of a signal, as in Neurometrics, which is a computerized quantitative analysis of brain electrical activity. In Neurometrics analysis, features are extracted from the quantitative electroencephalogram (QEEG and EP's). The features are then transformed to obtain Gaussianity, compared to age-expected normative values, and then expressed in standard deviation units of the normal population. The results may be displayed as color-coded topographic probability maps of brain function, or color-coded segments of a curve in the time domain (i.e., a graph of voltage vs. latency). Neurometric normative data is known to be free of ethnic bias. Utilizing these methods greatly enhances the sensitivity, specificity and clinical utility of such data. Profiles of QEEG and EP abnormalities can be mathematically described and are distinctive for different neuropsychiatric and neurological populations. A significant relationship between QEEG subtype membership established by cluster analysis, treatment outcome and evolution of disorders has also been established as described in U.S. Pat. No. 5,083,571, the entire disclosure of which is hereby expressly incorporated by reference herein.

In order to provide automatic evaluation of the filtered BAER, an algorithm will be developed which is applicable to fetal BAER to identify the latency of each peak by automatic peak-detection. After 3-point smoothing of the filtered average, the resulting BAER is amenable to automatic peak detection by a simple procedure, which searches for zero-values of the second derivative and prints the resulting series of time points. The computed peaks are marked on the optimally filtered BAER and superimposed on a normal template. FIG. 3 provides a good example; it shows the curve 100, which is a normal template, with the peaks of an abnormal BAER 101 marked by an '*'.

Once the normative data are available for the mean values of the voltages at every time point as a function of gestational age, this method can be used to test whether a fetal BAER is outside the limits of the distribution of the normal population. If an abnormality has a significance of probability ("P")>0.05, then its replication yields $P^2<0.0025$.

In order to assess BAER recorded from a fetus, the latencies are compared to normative data. Such normative data may be collected from a control group of pre-term and full-term infants shortly after birth and from pre-natal intra-uterine records collected from an adequate sample of mothers, for example, each week during the last trimester of pregnancies which result in the birth of a normal infant. The Neurometric norming approach, which has been demonstrated to greatly enhance the clinical utility of the EEG in various psychiatric and neurological disorders, may be applied to this data as well. This approach will rescale latency shifts as Z-score relative to the distribution of latencies of each peak in a reference normative database.

Preferably, the Subject Population for the collection of normative data will consist of fetuses in the last trimester of pregnancy, where the mothers of the subjects will be approximately between the ages of 25–35 years and with no history of any eventful or complicated pregnancies.

FBM 14 Use For Purposes Other Than Intra-uterine Monitoring

While FBM 14 is primarily intended for intra-uterine monitoring of the fetus from the time when the fetus' brain is capable of producing a detectable brainwave throughout labor, the FBM 14 can also be used to evaluate post-natal BAER in children of any age. The BAER would be digitally filtered and smoothed with automatic algorithms for peak detection as described above and analyzed using a table of expected BAER peak latency ranges installed in memory 23. Normative values for earlier detectable intra-uterine BAER may be determined by clinical trials and installed when tested and confirmed, in a manner substantially the same as that described above for obtaining other normative data. For the age range of 28 weeks to 1 year and above, Table 1 contains an example of normative values for mean latencies of Peaks I-V.

TABLE 1

(means and standard deviations are expressed in milliseconds)

| AGE RANGE | Peak I | Peak II | Peak III | Peak IV | Peak V |
|---|---|---|---|---|---|
| Gestation [28–40 weeks] | 2.8(0.6) | 3.6(0.8) | 5.2(0.8) | 6.5(0.9) | 7.8(0.6) |
| Full term [9 months] | 1.7(0.3) | 2.9(0.4) | 4.3(0.4) | 5.6(0.4) | 6.6(0.4) |
| 1 year and above | 1.5(0.2) | 2.7(0.2) | 3.8(0.2) | 5.1(0.3) | 5.9(0.3) |

In addition, the BAER data obtained from the fetus may be normalized against other earlier BAER recordings from the same fetus to construct a "self-norm" for the samples. Thus, fetal distress or infant auditory dysfunction may be flagged when a peak of the subject's BAER deviates from the reference value by a statistically significant amount, that is when the latency of any BAER peak is 2.56 standard deviations (P=0.0×0.01=0.0001) above the mean value of the population or self-norm reference distribution.

With complex algorithms and other methods disclosed in the present invention, it is possible to isolate and analyze the BAER of a fetus in-utero. The BAER of a fetus may provide an invaluable resource to obstetricians who may be able to detect a variety of hearing and developmental brain disorders of a fetus. In addition, the present invention provides an important tool to neural system researchers, since it allows the monitoring of the development of the neural system while the fetus is still in the uterus.

What is claimed is:

1. A method of monitoring a brain wave response of a fetus in utero, comprising the steps of:

(a) removably connecting an auditory transducer to an abdomen of a mother of the fetus;

(b) removably connecting at least one biosensor electrode to the mother's abdomen to detect brain wave activity in the fetus;

(c) pulsing the transducer with one of rectangular waves and tone pips of a selected frequency to emit pulsed audible sounds at predetermined times;

(d) detecting, for each pulsed audible sound, a series of voltage oscillations corresponding to brain stem auditory evoked responses (BAER) of the fetus which are time-locked to the corresponding audible sound; and (e) converting the BAER analog output to BAER digital data.

2. The method of monitoring as in claim 1, further comprising the steps of improving a signal to noise ratio of the BAER digital data using a computer-based QEEG (Quantitative EEG) system and passing the BAER digital data through a digital comb filter having a plurality of band pass frequency ranges within an overall frequency range of approximately 50–2000 Hz.

3. The method of monitoring as in claim 2, further comprising the steps of collecting a set of stimulus light averages of stimulus data during a stimulation period in which auditory stimuli are presented to the fetus and a set of noise light averages of noise data during a non-stimulation period in which no auditory stimuli are presented to the fetus, where each of the stimulus and noise light averages of data are generated over a plurality of trials.

4. The method according to claim 3, wherein each of the light averages comprises a plurality of EEG segments at least between 0.5 and 10 milliseconds in length sampled at least every 50 microseconds.

5. The method according to claim 4, wherein each of the trials comprises a plurality of EEG segments approximately 10 milliseconds in length.

6. The method according to claim 3, further comprising the steps of:

constructing both the stimulus and noise light averages of data in the time domain; and subjecting the light averages to analysis of frequency composition.

7. The method according to claim 6, wherein the light averages are subjected to one of spectral and wavelet analysis using one of a fast fourier transform (FFT) and a wavelet transform.

8. The method according to claim 7, wherein the FFT is a multipoint FFT and wherein an initial set of points span an analysis epoch of the BAER and the remaining points are set to a mean value of the initial points.

9. The method according to claim 8, wherein the FFT is a 512 point FFT and wherein the initial set comprises approximately 200 points spanning an approximately 10 millisecond analysis epoch of the BAER.

10. The method according to claim 7, further comprising the steps of:

determining an amplitude and phase for one of spectral and wavelet components for each of the trials;

computing mean amplitude and phase variances for each of the one of spectral and wavelet components of the stimulus set of data;

computing separately from the computations for the stimulus set of data mean amplitude and phase variances for each of the one of spectral and wavelet components of the noise set of data; and computing for each of the one of spectral and wavelet components an F ratio of phase variance in the stimulus set of data to phase variance in the noise set of data.

11. The method according to claim 10, further comprising the steps of:

identifying significant components of the one of spectral and wavelet components for which the F ratio exceeds a predetermined threshold;

setting to zero components not identified as significant; and performing one of an IFFT and a wavelet sum on the significant components.

12. The method according to claim 11, further comprising the step of computing, after the digital filtering and IFFT have been performed, mean amplitudes and variances of amplitude at each sampling point across the set of light averages.

13. The method according to claim 12, further comprising the step of smoothing the data to reduce the number of peaks to a group of major peaks each separated by a predetermined minimum amount of time corresponding to an expected transmission delay between brainstem nuclei.

14. The method according to claim 12, further comprising the step of comparing the BAER data to control data obtained from one of a control group of fetuses and self-norm data collected from the same fetus during a reference period during an earlier stage of development.

15. The method according to claim 11, further comprising the step of locating latencies of successive peaks of the BAER by one of a zero crossing of a first derivative of the data, minimum valves of a second derivative of the data and directly from the FFT.

16. The method according to claim 15, wherein the minimum amount of time is no less than a critical value.

17. The method according to claim 16, wherein the critical value is approximately 0.70 milliseconds.

18. The method according to claim 15, further comprising the steps of:

computing a coefficient of variation (CV) as a ratio of variance to mean amplitude at each sampling point for each of the trials; and locating successive BAER peaks by one of identifying points at which values of CV are below a predetermined value and identifying points at which a first derivative of a plot of CV is zero.

19. The method according to claim 18, wherein the entire method is performed twice and repeated data from the repeated performance is compared to original data to determine validity of the results.

20. The method according to claim 19, wherein peak locations from the updated and self-norm data are compared and wherein at least a plurality of peaks must be within a predetermined latency margin of one another, to estimate whether progressive changes are taking place.

21. The method according to claim 18, wherein threshold values of CV from control or Self-norm reference BAER data are stored in a memory and are compared to the computed CV values to determine validity of the current data.

22. The method according to claim 21, wherein the current BAER data are combined with previous measurements of the same subject to generate a self-norm.

* * * * *